(12) United States Patent
Stora et al.

(10) Patent No.: US 6,774,101 B2
(45) Date of Patent: Aug. 10, 2004

(54) ALCOHOL-FREE PERFUMING COMPOSITION

(75) Inventors: Thierry Stora, Sergy (FR); Aude Daugeron, Rueil-Malmaison (FR); Rémy Mounier, Aulnay sur Mauldre (FR); Nathalie Personnic, Annemasse (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 10/167,292

(22) Filed: Jun. 10, 2002

(65) Prior Publication Data

US 2003/0007986 A1 Jan. 9, 2003

Related U.S. Application Data

(63) Continuation of application No. PCT/IB01/01961, filed on Oct. 17, 2001.

(30) Foreign Application Priority Data

Oct. 20, 2000 (CH) ............................................. 2060/00

(51) Int. Cl.⁷ ................................................. A61K 7/46
(52) U.S. Cl. ................................ 512/1; 516/53; 516/72
(58) Field of Search ............................... 512/1; 516/53, 516/72

(56) References Cited

U.S. PATENT DOCUMENTS

| | | | |
|---|---|---|---|
| 5,252,555 A | 10/1993 | Dartnell et al. ................. | 512/4 |
| 5,320,863 A | 6/1994 | Chung et al. ................. | 426/650 |
| 5,374,614 A | 12/1994 | Behan et al. .................. | 512/3 |
| 5,389,607 A | 2/1995 | Dartnell et al. ................. | 512/3 |
| 5,468,725 A * | 11/1995 | Guenin et al. .................. | 512/2 |
| 5,585,343 A | 12/1996 | McGee et al. .................. | 512/1 |
| 5,753,241 A | 5/1998 | Ribier et al. ................. | 424/401 |

FOREIGN PATENT DOCUMENTS

| | | |
|---|---|---|
| EP | 0 516 508 A1 | 12/1992 |
| EP | 0 572 080 A1 | 1/1993 |
| EP | 0 571 677 A1 | 12/1993 |
| EP | 0 728 460 B1 | 8/1997 |
| FR | 2 703 926 | 10/1994 |
| JP | 8 225 429 | 9/1996 |

* cited by examiner

*Primary Examiner*—Jill Warden
*Assistant Examiner*—Monique T. Cole
(74) *Attorney, Agent, or Firm*—Winston & Strawn LLP

(57) ABSTRACT

The invention relates to an alcohol-free translucent perfuming composition in the form of a low viscosity, vaporizable oil-in-water emulsion containing at least a perfuming ingredient, a surfactant system having a hydrophilic-lipophilic ratio not less than 10 and water. The composition has been optimized so as to include significant amounts of perfume. The emulsion is also characterized by the variation of the average size of its drops during the month following its formulation, at a temperature of 45° C. and ranging between 0.1 and 30 nm.

16 Claims, No Drawings

ALCOHOL-FREE PERFUMING COMPOSITION

CROSS-REFERENCE TO RELATED APPLICATIONS

This application is a continuation of the US national stage designation of International application PCT/IB01/01961 filed Oct. 17, 2001, the content of which is expressly incorporated herein by reference thereto.

TECHNICAL FIELD

The present invention relates to the perfume industry. It relates more particularly to an alcohol-free concentrated perfuming composition in the form of a translucent oil-in-water emulsion. This perfuming composition can be used in particular in the form of a perfumed emulsion capable of being atomized onto the skin or hair, on to quite different types of surfaces, or simply into the ambient air.

PRIOR ART

Oil-in-water emulsions are well known in the cosmetics industry and in dermatology, in particular for the preparation of cosmetic products such as creams, lotions, tonics or serums. Emulsions such as this are for example described in European patent EP 728 460, which relates more particularly to transparent nanoemulsions based on non-ionic amphiphilic liquid lipids and their use in cosmetics and dermopharmacy. These emulsions always contain a small proportion of a low-molecular-weight alcohol.

The problems associated with the formulation of emulsions in the cosmetics industry are not the same as those encountered in perfumery. The objective of hair-care and skin-care products and of products for cleaning the hair and skin is to optimize the penetration of active substances into the superficial layers of the skin. Moreover, these cosmetic emulsions are of a highly specific composition and are characterized in particular by the fact that their oil phase comprises a large variety of active substances such as natural or synthetic oils, hydrocarbons, halogenated hydrocarbons, mineral acid esters or silicones, differing according to the desired application. In contrast with a cosmetic composition, a perfuming composition is a perfume carrier the primary function of which is to impart a scent to a product. In the form of an emulsion, its oil phase is made up essentially of perfuming ingredients. It will be easily understood that the problems to be resolved when formulating emulsions, such as in particular optimization of the parameters capable of influencing the stability of the product, are posed differently in different industries. The solutions to these problems in fact depend on the desired objective for the product and more precisely on the composition of the continuous and dispersed phases, and therefore cannot be applied to perfumery simply on the analogy of fields such as cosmetics or dermatology. The problems of stability specific to the emulsification of a perfume are moreover well known in the perfume industry (see the magazine Cosmetics and Toiletries®, vol. 109, pages 71–75, 1994) and relate to the nature of the emulsified ingredients, i.e., the perfuming ingredients.

Furthermore, apart from having chemical stability, an emulsion must also meet certain requirements regarding physical stability. For example, one of the phenomena typically associated with the physical instability of an emulsion is the ascending and descending movement of the dispersed droplets relative to the continuous phase. These phenomena are called creaming or sedimentation, respectively.

Microemulsions are dispersed systems which provide a solution to the problems of destabilization which, in the case of a conventional emulsion, lead to phase separation. These systems are widely described in the prior art, for example in patent applications or patents such as EP 516 508; EP 572 080; U.S. Pat. Nos. 5,320,863; 5,585,343 or FR 2,703,926. These documents all describe dispersions of oil and water that are homogeneous, transparent and stable, with these properties originating from the large quantities of added surfactants and co-surfactants.

Microemulsions and emulsions constitute two disperse systems of very distinct types. Whereas emulsions are unstable systems, microemulsions are stable and form spontaneously when oil, water, surfactants and co-surfactants are mixed together. The thermodynamic stability of a microemulsion is revealed in particular by the fact that, in contrast with an emulsion, the mean droplet size in the system does not vary over time. The two disperse systems also differ in respect of their optical properties, microemulsions having a mean droplet size much less than the wavelength of light and a relatively narrow droplet-size distribution. This type of formulation thus diffuses light only slightly and is consequently transparent, while emulsions have a droplet size comparable to or greater than the wavelength of visible light and a broader droplet-size distribution so they diffuse light, thus yielding an optical effect ranging from milky to translucent.

In any case, it is very clear to the person skilled in the art who is familiar with the different types of disperse systems that emulsions and microemulsions constitute two very different systems.

Now, the aim of the present invention is to create in particular compositions which do not incorporate large quantities of surfactants relative to the quantity of perfuming ingredients, the presence of surfactants considerably limiting the proportion of perfume that can be added to the mixture. This is why a disperse system of the microemulsion type is unsuitable for the present invention, which therefore relates to a product in the form of an oil-in-water emulsion which, its nature notwithstanding, nevertheless possesses quite surprising physical stability.

Another problem specific to the perfume industry is that of the typical presence of alcohol. Ethanol is very widely used as a solvent in the preparation of perfumed compositions such as perfumes, eaux de toilette, eaux de Cologne, or deodorising compositions for example. Ethanol enables good solubilization of the perfuming ingredients available to the perfumer. It thus constitutes the principle vector used in perfumed body-care products (perfumes, eaux de toilette, deodorants, after-shaves etc.) and, as it is virtually odorless, it is a very good solvent which evaporates rapidly thus imparting a cooling sensation. For these reasons, the majority of commercially available perfuming compositions contain ethanol, generally in a proportion of 50 to 95% by volume.

However, ethanol is significantly volatile, and it is sometimes desirable to obtain perfuming compositions with a very low, or even a zero alcohol content.

On the international market, there currently is a trend towards alcohol-free perfumes, with this trend arising both from the regulation of VOCs (volatile organic compounds) as well as from the preference of the consumer for alcohol-free products intended for sensitive skins and which can be used safely in sunlight.

Japanese patent application JP 96225429 discloses perfuming compositions which, despite being designated "alcohol-free", generally always contain a small proportion of alcohol. This application describes perfuming compositions which are either liquid or in the form of a gel, and comprise in particular water-soluble polymers such as gums. These type polymers, which are well-known in relation to emulsions, are used as a stabilizing agent. However, it is also known that the use of these polymers has the disadvantage of rendering emulsions sticky to the touch. These constituents furthermore have the effect of considerably increasing the viscosity of the emulsions in which they are contained. The cited Japanese patent application also states that the products obtained are sometimes viscous or even in the form of gels.

The present invention proposes to solve the problem of obtaining a perfuming product in the form of a translucent alcohol-free emulsion which is atomizable and capable of containing a large proportion of perfume, is of a pleasing appearance and pleasant to the touch, as well as having good long-term stability. No document of the prior art describes emulsions such as this, meaning that it has not yet been possible to solve the problem posed.

SUMMARY OF THE INVENTION

The present invention provides a solution to the various problems mentioned, by means of an alcohol-free perfuming composition in the form of an atomizable, translucent oil-in-water emulsion containing at least one perfuming ingredient, a surfactant system having a hydrophilic-lipophilic balance (HLB) greater than or equal to 10, and water. Perfuming composition is used herein to mean a composition the primary function of which is to modify the odor of a product or to impart an odor to a product or a person. The composition of the invention has been optimized so as to be able to contain large quantities of perfume, that is, between 0.1 and 18% by weight relative to the total weight of the emulsion. The emulsion is also very stable, as shown by the variation in the mean droplet size in the first month following its formulation, wherein this variation is within the range of 0.1 to 30 nm at a temperature of 45° C.

The emulsion forming the subject of the present invention has numerous advantages for its intended use. Firstly, as mentioned above, this composition—which is intended in particular to be atomized onto the skin or hair, onto quite different types of surfaces to be perfumed, or simply into the ambient air—contains a particularly high concentration of perfuming ingredients.

Secondly, the mean droplet size is such that the emulsion advantageously satisfies the desired stability criteria (i.e., the absence of the creaming or sedimentation effects) without requiring the presence of stabilizing agents such as water-soluble polymers, as is the case in the prior art. The absence of these constituents has the advantage of providing a substance of low viscosity which is atomizable and non-sticky to the touch. The viscosity of the compositions according to the invention is preferably below 1 Pa.s.

Moreover, the mean droplet size of the emulsion exerts an optical effect on the end product, the translucent appearance of which with its bluish shimmer is greatly liked by the consumer and is especially well adapted to a use for perfume-derived products, such as atomizable perfume emulsions. Generally, the optical properties of the compositions of the invention are characterized by a transmission varying between 10 and 90% when measured at a wavelength of 600 nm at 25° C. in a cell with a thickness of 1 cm.

Other advantages will appear in the course of the detailed description of the invention and via the examples cited for illustration purposes.

DETAILED DESCRIPTION OF THE PREFERRED EMBODIMENTS

The disperse phase of the emulsion forming the subject of the invention is essentially composed of perfuming ingredients. More particularly, it comprises perfuming ingredients in a proportion of 50 to 99% by weight. The latter are present in a quantity varying between 0.1 and 18% by weight relative to the total weight of the emulsion, and preferably constitute between 1 and 15% by weight relative to the total weight of the emulsion, or even between 6 and 10% by weight relative to the total weight of the emulsion.

The perfuming ingredients usable according to the invention are ingredients currently in use in perfumery. Their nature does not call for a more detailed description here, which in any case could never be exhaustive as the person skilled in the art is in a position to choose them on the basis of his or her general knowledge and depending on the desired olfactory effect. These perfuming ingredients belong to chemical classes as varied as the alcohols, aldehydes, ketones, esters, ethers, acetates, nitrites, terpenic hydrocarbons, nitrogen- or sulfur-containing heterocyclic compounds, as well as natural or synthetic essential oils. Moreover, many of these ingredients are listed in reference texts such as S. Arctander's book Perfume and Flavor Chemicals, 1969, Montclair, N.J., USA or its more recent editions, or in other works of a similar nature, as well as in more recent scientific and patent literature relating to the art of perfumery.

The stability of the perfuming compositions of the invention is fully evaluable and is matched to the typical storage periods of products of this type, due in particular to the presence of a surfactant system the hydrophilic-lipophilic balance (HLB) of which is greater than or equal to 10, preferably greater than or equal to 15. Surfactant system is here used to mean a single surfactant or a mixture of two or more agents of this type. The surfactant system according to the invention proves especially advantageous in that it yields a stable emulsion for a great variety of perfuming ingredients used in the oil phase of the emulsion. Indeed, even when the perfuming ingredients have very varied hydrophilic and hydrophobic characteristics, we have discovered that the surfactant system of the invention remain suitable for a great variety of perfuming ingredients used and yields an emulsion which satisfies the stability criteria necessary for storing the product.

The surfactant system used according to the invention comprises polyethoxylated or polypropoxylated non-ionic surfactants. The surfactant system used according to the invention is preferably composed of at least one non-ionic surfactant belonging to one of the families containing the polyethylene glycol stearyl ethers, the polyethylene glycol (n) oleyl ethers, the polyethylene glycol (n) nonylphenyl ethers, and the polysorbates. Other polyethylene glycol alkyl ethers may be used according to the invention. The use of mixtures of these surfactants has proved especially advantageous.

The HLB value of the system must be greater than or equal to 10. In accordance with one embodiment of the invention, a surfactant system is used which is constituted by an agent selected from among the family of the polyethylene glycol (n) stearic ethers. A mixture of Steareth-20 and Steareth-21 with an HLB value of 15.3 is preferably used. Good results have also been obtained with the use of Oleth-20 (HLB=15.3).

The surfactant system according to the invention is used in proportions of between 0.1 and 18%, preferably between 1 and 10% by weight relative to the total weight of the emulsion. The best results have been obtained by using 3 to 8% by weight of surfactant.

As stated above, the oil phase of the oil-in-water emulsion of the invention consists essentially of perfuming ingredients. Other substances may also be present in the oil phase and have given good results. One may cite in particular the heavy paraffins such as eicosane, containing 20 carbon atoms, or the fractions of isoparaffin marketed under the name Isopar®, for example Isopar® V by Exxon Chemicals, or another fraction of paraffin, Gemseal 60 marketed by Total. These substances are used as emulsion stabilisers.

The variation over time of the mean droplet size of the emulsion of the invention constitutes an essential characteristic of the perfuming composition. This variation, though highly characteristic of the emulsion as a thermodynamically unstable disperse system, is nevertheless sufficiently small to render the product highly advantageous in the sense that the current destabilization phenomena such as the creaming effect or sedimentation are avoided. This variation can in particular be measured by a method of dynamic diffusion of light (described in detail in Example 1), which enables one to establish that, in the course of the first month following formulation of the emulsion according to the invention, the variation in the mean droplet size of the system, at a temperature of 45° C., is within the range 0.1 to 30 nm.

The perfuming compositions according to the invention can be used for different types of applications for perfumery products such as alcohol-free perfume emulsions, eaux de toilette or eaux de Cologne, atomizable on to the skin or hair. They may also serve to perfume surfaces of other types such as fabrics, wood or glass. In another embodiment, the compositions of the invention may even perfume the ambient air and thus be used as perfume diffusers.

The preparation of the emulsions according to the invention will be described in detail in the following examples.

EXAMPLES

The invention will now be illustrated by means of the following non-limiting examples, in which temperatures are indicated in degrees Celsius, the proportions of the compounds are given in % by weight, and the abbreviations have the conventional meaning used in the art.

Example 1
Preparation of an Alcohol-Free Perfuming Composition in the Form of a Translucent, Atomizable Oil-In-Water Emulsion

| Ingredients | Parts by weight |
| --- | --- |
| Perfuming base* | 8.00 |
| Brij ® 98V[1)] | 8.00 |
| Isopar ® V[2)] | 4.00 |
| Water | 80.00 |
| Total | 100.00 |

[1)]Oleth-20; origin: Uniqema, Netherlands
[2)]origin: Exxon Chemicals, USA
*The perfuming base was obtained by mixing the following ingredients:
| | |
| --- | --- |
| Citronellyl acetate | 3 |
| Geranyl acetate | 9 |
| Linalyl acetate | 276 |
| 10% *C10 aldehyde | 3 |

| Ingredients | Parts by weight |
| --- | --- |
| 10% *C12 aldehyde | 12 |
| Methyl anthranilate | 16 |
| Essence of bergamot | 226 |
| Cetalox ®[1)] | 5 |
| Essence of lemon | 318 |
| Dihydromyrcenol[2)] | 60 |
| Dipropylene glycol | 20 |
| 10% *Elemi[3)] | 20 |
| Lilial ®[4)] | 3 |
| Ethyl linalol | 66 |
| 10% *3-(4-Methoxyphenyl)-2-methylpropanal[5)] | 30 |
| Geraniol | 6 |
| 50% *Habanolide ®[6)] | 130 |
| Hedione ®[7)] | 215 |
| Hedione ® HC[8)] | 72 |
| 10% **Indole | 12 |
| Iso E super[9)] | 85 |
| Essence of lavandin grosso | 26 |
| 1% *Liffarome ®[10)] | 20 |
| Linalol | 40 |
| Essence of mandarin sfuma | 5 |
| 10% *Essence of spearmint | 30 |
| Essence of bitter orange neroli | 130 |
| Essence of Portugal Floride orange | 80 |
| Phenethylol | 9 |
| Essence of petitgrain | 63 |
| Pipol | 5 |
| Essence of rosemary | 16 |
| Terpineol | 9 |
| Essence of violet | 50 |
| 1% *Zestover[11)] | 30 |
| Total | 2100 |

*in dipropylene glycol (DIPG)
**in triethanolamine
[1)]8,12-epoxy-13,14,15,16-tetranorlabdane; origin: Firmenich SA, Geneva, Switzerland
[2)]origin: International Flavors & Fragrances, USA
[3)]5-allyl-1,2,3-trimethoxybenzene; origin: Calchauvet, Grasse, France
[4)]3-(4-tert-butylphenyl)-2-methylpropanal; origin: Givaudan-Roure SA, Vernier, Switzerland
[5)]origin: Firmenich SA, Geneva, Switzerland
[6)]pentadecenolide; origin: Firmenich SA, Geneva, Switzerland
[7)]Methyl dihydrojasmonate; origin: Firmenich SA, Geneva, Switzerland
[8)]Methyl dihydrojasmonate with a high content of the cis-isomer; origin: Firmenich SA, Geneva, Switzerland
[9)]origin: International Flavors & Fragrances, USA
[10)]3-hexenylmethyl carbonate; origin: International Flavors & Fragrances, USA
[11)]2,4-dimethyl-3-cyclohexene-1-carbaldehyde; origin: Firmenich SA, Geneva, Switzerland Method of Preparing the Emulsion The liquidised surfactant system and the oil phase were mixed at ambient temperature until a homogeneous mixture was obtained, after which the aqueous phase was added. The mixture was then heated so as to obtain a coarse emulsion, while maintaining slight stirring (200 rpm). While the temperature was increasing, the emulsion became finer and then more viscous. The heating was then stopped and the emulsion was cooled to ambient temperature (25°), still with stirring.

A finely disperse oil-in-water emulsion with a blue-shimmering translucent appearance was obtained (80% transmission at a wavelength of 600 nm and a temperature of 25°, in a cell with a thickness of 1 cm). The size of the particles was measured with the aid of a granulometer (Autosizer 4700, origin: Malvern; angle of measurement:

90°; laser wavelength: 532 nm; measuring temperature: 25°; method of analysis monomodal in intensity). The mean particle size of the present emulsion was 29.5 nm after formulation. After a month at 45° the mean droplet size had varied by 20 nm.

Example 2

Preparation of an Alcohol-Free Perfuming Composition in the Form of a Translucent Atomizable Oil-In-Water Emulsion

| Ingredients | Parts by weight |
|---|---|
| Perfuming base* | 8.00 |
| Brij ® 98V[1)] | 8.00 |
| Isopar ® V[2)] | 4.00 |
| Water | 80.00 |
| Total | 100.00 |

[1)]See Example 1
[2)]See Example 1
*The perfuming base was obtained by mixing the following ingredients:

| Benzyl acetate | 250 |
|---|---|
| Pipol acetate | 70 |
| Styrallyl acetate | 230 |
| Phenylacetaldehyde | 10 |
| Ambrettolide ®[1)] | 10 |
| Astrotone | 300 |
| Bergamot essence | 1160 |
| β-Ionone | 550 |
| Essence of black currant | 150 |
| 50% *Cetalox ®[2)] | 60 |
| Essence of lemon | 850 |
| Citronellol | 210 |
| Damascenone | 20 |
| 4-Decanolide | 20 |
| Dihydromyrcenol[3)] | 440 |
| Dipropylene glycol | 20 |
| Ethyl linalol | 720 |
| 7-Methyl-2H,4H-1,5-benzodioxepin-3-one[4)] | 100 |
| Floralozone ®[5)] | 50 |
| 3-(4-Methoxyphenyl)-2-methylpropanal[4)] | 170 |
| Fructone ®[6)] | 100 |
| Galbex ®[4)] | 50 |
| γ-Damascone | 5 |
| Essence of geranium | 30 |
| Essence of grapefruit | 100 |
| Habanolide ®[7)] | 1120 |
| Hedione ®[8)] | 2890 |
| Hedione ® HC[9)] | 950 |
| Heliopropanal[10)] | 400 |
| Indole | 35 |
| Iso E Super[11)] | 380 |
| Essence of lavandin grosso | 40 |
| Liffarome ®[12)] | 1 |
| Lilial ®[13)] | 1050 |
| Lyral ®[14)] | 430 |
| Essence of mandarin sfuma | 270 |
| Melonal[15)] | 3 |
| Essence of spearmint | 20 |
| Peony HS (HeadSpace)[4)] | 260 |
| Phenethylol | 80 |
| Phenylhexanol | 50 |
| Pipol | 20 |
| Essence of orange | 500 |
| Rosalva[16)] | 4 |
| Benzyl salicylate | 400 |
| Pipol salicylate | 400 |

-continued

| Ingredients | Parts by weight |
|---|---|
| 10% **BHT | 200 |
| Zestover[17)] | 22 |
| Total | 15200 |

*in 2-(2-ethoxyethoxy)-1-ethanol
**in dipropylene glycol
[1)]origin: Givaudan-Roure SA, Vernier, Switzerland
[2)]8,12-epoxy-13,14,15,16-tetranorlabdane: origin: Firmenich SA, Geneva, Switzerland
[3)]origin: International Flavors & Fragrances, USA
[4)]origin: Firmenich SA, Geneva, Switzerland
[5)]3-(4-ethylphenyl)-2,2-dimethylpropanal + 3-(2-ethylphenyl)-2,2-dimethylpropanal; origin: International Flavors & Fragrances, USA
[6)]2-methyl-1,3-dioxolane-2-ethyl acetate; origin: International Flavors & Fragrances, USA
[7)]pentadecenolide; origin: Firmenich SA, Geneva, Switzerland
[8)]methyl dihydrojasmonate; origin: Firmenich SA, Geneva, Switzerland
[9)]methyl dihydrojasmonate with a high content of the cis-isomer; origin: Firmenich SA, Geneva, Switzerland
[10)]3-(1,3-benzodioxol-5-yl)-2-methylpropanal; origin: Firmenich SA, Geneva, Switzerland
[11)]origin: International Flavors & Fragrances, USA
[12)]3-hexenylmethyl carbonate; origin: International Flavors & Fragrances, USA
[13)]3-(4-tert-butylphenyl)-2-methylpropanal; origin: Givaudan-Roure SA, Vernier, Switzerland
[14)]4-(4-hydroxy-4-methylpentyl)-3-cyclohexene-1-carbaldehyde + 3-(4-hydroxy-4-methylpentyl)-3-cyclohexene-1-carbaldehyde; origin: International Flavors & Fragrances, USA
[15)]2,6-dimethyl-5-heptanal; origin: Givaudan-Roure SA, Vernier, Switzerland
[16)]9-decen-1-ol; origin: International Flavors & Fragrances, USA
[17)]2,4-dimethyl-3-cyclohexene-1-carbaldehyde; origin: Firmenich SA, Geneva, Switzerland The emulsion was prepared in a way similar to that prepared in Example 1.

A translucent emulsion was obtained (69.4% transmission at a wavelength of 600 nm, a temperature of 25°, in a cell with a thickness of 1 cm), having a mean particle size of 30 nm after formulation. After one month at 45°, the mean particle size had varied by 19 nm.

Example 3

Preparation of an Alcohol-Free Perfuming Composition in the Form of a Translucent, Atomizable Oil-In-Water Emulsion

| Ingredients | Parts by weight |
|---|---|
| Perfuming base* | 8.00 |
| Brij ® 78P[1)] | 7.00 |
| Brij ® 721[2)] | 1.00 |
| Gemseal 60[3)] | 4.00 |
| Water | 80.00 |
| Total | 100.00 |

*see Example 2
[1)]Steareth-20; origin: Uniqema, Netherlands
[2)]Steareth-21; origin: Uniqema, Netherlands
[3)]origin: Total, France The emulsion was prepared in a way similar to that prepared in Example 1.

The composition obtained was translucent (67.5% transmission at 600 nm, at a temperature of 25°, in a cell with a thickness of 1 cm). The mean particle size was 36.5 nm after formulation and its variation after one month at 45° was 1 nm.

Example 4

Preparation of an Alcohol-Free Perfuming Composition in the Form of a Translucent, Atomizable Oil-In-Water Emulsion

| Ingredients | Parts by weight |
|---|---|
| Perfuming base* | 8.00 |
| Brij ® 78P[1)] | 6.00 |
| Brij ® 721[2)] | 2.00 |
| Gemseal 60[3)] | 4.00 |
| Water | 80.00 |
| Total | 100.00 |

*see Example 2
[1)]Steareth-20; origin: Uniqema, Netherlands
[2)]Steareth-21; origin: Uniqema, Netherlands
[3)]origin: Total, France The emulsion was prepared in a way similar to that prepared in Example 1.

The composition obtained was translucent (74.4% transmission at 600 nm, a temperature of 25°, in a cell with a thickness of 1 cm). The mean particle size was 37.5 nm after formulation, and its variation after one month at 45° was 2 nm.

Example 5
Preparation of an Alcohol-Free Perfuming Composition in the Form of a Translucent, Atomizable Oil-In-Water Emulsion

| Ingredients | Parts by weight |
|---|---|
| Perfuming base* | 8.00 |
| Brij ® 78P[1)] | 4.00 |
| Brij ® 721[2)] | 4.00 |
| Gemseal 60[3)] | 4.00 |
| Water | 80.00 |
| Total | 100.00 |

*see Example 2
[1)]Steareth-20; origin: Uniqema, Netherlands
[2)]Steareth-21; origin: Uniqema, Netherlands
[3)]origin: Total, France The emulsion was prepared in a way similar to that prepared in Example 1.

The composition obtained was translucent (45.7% transmission at 600 nm, a temperature of 25°, in a cell with a thickness of 1 cm). The mean particle size was 46 nm after formulation, and its variation after one month at 45° was 0.5 nm.

What is claimed is:

1. An alcoholic-free perfuming composition in the form of a translucent, atomizable oil-in-water emulsion consisting essentially of at least one perfuming ingredient, a non-ionic surfactant system and water, wherein the perfuming ingredient is present in an amount of between 0.1 and 18% by weight relative to the total weight of the composition, the surfactant system has a hydrophilic-lipophilic balance (HLB) greater than or equal to 10, and the emulsion has a mean droplet size variation that is in the range of 0.1 to 30 nm at a temperature of 45° C. for at least one month.

2. The perfuming composition according to claim 1, wherein the emulsion has a viscosity of less than 1 Pa.s.

3. The perfuming composition according to claim 1, having an optical transmission through the composition in a cell having a thickness of 1 cm of between 10 and 90% measured at a wavelength of 600 nm and a temperature of 25° C.

4. The perfuming composition according to claim 1, wherein the perfuming ingredient is present in an amount of between 1 and 15% by weight relative to the total weight of the composition.

5. The perfuming composition according to claim 4, wherein the perfuming ingredient is present in an amount of between 6 and 10% by weight relative to the total weight of the composition.

6. An alcohol-free perfuming composition in the form of a translucent, atomizable oil-in-water emulsion containing at least one perfuming ingredient, a surfactant system and water, wherein the perfuming ingredient is present in an amount of between 0.1 and 18% by weight relative to the total weight of the composition, the surfactant system has a hydrophilic-lipophilic balance (HLB) greater than or equal to 10, and the emulsion has a mean droplet size variation that is in the range of 0.1 to 30 nm at a temperature of 45° C. for at least one month, wherein the emulsion has an oil phase composed of perfuming ingredients in a proportion of 50 to 99% by weight.

7. The perfuming composition according to claim 1, wherein the surfactant system has a hydrophilic-lipophilic balance that is greater than or equal to 15.

8. The perfuming composition according to claim 1, wherein the non-ionic surfactant system comprises at least one polyethoxylated or polypropoxylated non-ionic surfactant.

9. The perfuming composition according to claim 8, wherein the polyethoxylated non-ionic surfactant is a polyethylene glycol stearyl ether, a polyethylene glycol oleyl ether, a polyethylene glycol nonylphenyl ether, or a polysorbate.

10. An alcohol-free perfuming composition in the form of a translucent, atomizable oil-in-water emulsion at least one perfuming ingredient, a surfactant system and water, wherein the perfuming ingredient is present in an amount of between 0.1 and 18% by weight relative to the total weight of the composition, the surfactant system has a hydrophilic-lipophilic balance (HLB) greater than or equal to 10, and the emulsion has a mean droplet size variation that is in the range of 0.1 to 30 nm at a temperature of 45° C. for at least one month, wherein the surfactant system comprises a polyethylene glycol oleyl ether or a mixture of polyethylene glycol stearic ethers.

11. The perfuming composition according to claim 10, wherein the surfactant system comprises a mixture of polyethylene glycol stearic ethers.

12. The perfuming composition according to claim 1, wherein the surfactant system represents 0.1 to 18% by weight of the total weight of the composition.

13. The perfuming composition according to claim 12, wherein the surfactant system represents 3 to 8% by weight of the total weight of the composition.

14. The perfuming composition according to claim 1, in the form of an alcohol-free emulsion of perfume, eau de toilette or eau de Cologne, atomizable on to the skin or hair.

15. The perfuming composition according to claim 1, in the form of an emulsion atomizable on to any type of surface or into the ambient air.

16. The perfuming composition according to claim 10, wherein the surfactant system consists essentially of a polyethylene glycol oleyl ether.

* * * * *

UNITED STATES PATENT AND TRADEMARK OFFICE
CERTIFICATE OF CORRECTION

PATENT NO. : 6,774,101 B2
DATED : August 10, 2004
INVENTOR(S) : Stora et al.

It is certified that error appears in the above-identified patent and that said Letters Patent is hereby corrected as shown below:

Column 9,
Line 48, change "An alcoholic-free perfuming composition" to -- An alcohol-free perfuming composition --.

Column 10,
Line 33, after "atomizable oil-in-water emulsion" insert -- comprising --.

Signed and Sealed this

Fourteenth Day of December, 2004

JON W. DUDAS
*Director of the United States Patent and Trademark Office*